(12) United States Patent
Karlsson et al.

(10) Patent No.: US 8,876,781 B2
(45) Date of Patent: Nov. 4, 2014

(54) SAFETY PEN NEEDLE DEVICE

(75) Inventors: Sebastian Karlsson, Sundbyberg (SE);
Lennart Brunnberg, Tyresö (SE);
Carlos Guillermo, Atascadero, CA (US)

(73) Assignee: SHL Group AB, Nacka Strand (SE)

( * ) Notice: Subject to any disclaimer, the term of this patent is extended or adjusted under 35 U.S.C. 154(b) by 368 days.

(21) Appl. No.: 13/378,948

(22) PCT Filed: Jul. 5, 2010

(86) PCT No.: PCT/SE2010/050771
§ 371 (c)(1),
(2), (4) Date: Mar. 1, 2012

(87) PCT Pub. No.: WO2010/147552
PCT Pub. Date: Dec. 23, 2010

(65) Prior Publication Data
US 2012/0150125 A1    Jun. 14, 2012

Related U.S. Application Data

(60) Provisional application No. 61/218,216, filed on Jun. 18, 2009.

(30) Foreign Application Priority Data

Aug. 21, 2009  (SE) ...................... 0950597

(51) Int. Cl.
*A61M 5/32*   (2006.01)
(52) U.S. Cl.
CPC ............ *A61M 5/326* (2013.01); *A61M 5/3271* (2013.01); *A61M 2005/3247* (2013.01); *A61M 2005/3254* (2013.01); *A61M 2005/3267* (2013.01)
USPC ........................................ 604/198; 604/110

(58) Field of Classification Search
USPC ................................................ 604/110, 198
See application file for complete search history.

(56) References Cited

U.S. PATENT DOCUMENTS

2008/0077093 A1*  3/2008  Gratwohl et al. ............. 604/198
2008/0177237 A1*  7/2008  Stonehouse et al. .......... 604/263
(Continued)

FOREIGN PATENT DOCUMENTS

WO    2010/147552 A1    12/2010

OTHER PUBLICATIONS

Request to Restore Priority in PCT/2010/050771, Jul. 5, 2010.
(Continued)

*Primary Examiner* — Nicholas Lucchesi
*Assistant Examiner* — Anh Bui
(74) *Attorney, Agent, or Firm* — Piedmont Intellectual Property

(57) ABSTRACT

The present invention relates to a safety pen needle device comprising a first needle shield (60) and a second back-end needle shield (90). During the injection the first needle shield (60) is moved to en retracted position this movement causes a actuation sleeve (31) to rotate. Said rotation causes a holding member (96, 98) provided on the second needle shield (90) to be released. When the first needle shield (60) is moved from the retracted position to a extended position the actuation sleeve (31) is rotated further so that a first guide member (74) on the first needle shield (60) abuts a first stop member (34) arranged on said actuation sleeve (31). After an performed injection both shields are moved to extended positions by the rotation of an actuation sleeve (31). After the injection the shield are locked it their extended position.

7 Claims, 11 Drawing Sheets

(56) References Cited

U.S. PATENT DOCUMENTS

2008/0177238 A1    7/2008  Follman et al.
2009/0227950 A1*  9/2009  Jensen et al. ............ 604/110
2011/0178473 A1*  7/2011  Richards et al. .......... 604/198

OTHER PUBLICATIONS

Swedish Patent Office, Notice of Intended Refusal of Request to Restore Priority in PCT/2010/050771, Jul. 19, 2010.

Swedish Patent Office, Decision on Request to Restore Priority in PCT/2010/050771, Sep. 27, 2010.

Swedish Patent Office, Int'l Search Report in PCT/SE2010/050771, Sep. 28, 2010.

Swedish Patent Office, Written Opinion in PCT/SE2010/050771, Sep. 28, 2010.

* cited by examiner

SAFETY PEN NEEDLE DEVICE

TECHNICAL AREA

The present invention relates to a safety pen needle device to be used with a medicament delivery device and in particular a safety pen needle providing added security against accidental needle sticks.

TECHNICAL BACKGROUND

Accidental needle sticks from used and thereby contaminated needles expose both hospital personnel and other persons that come in contact with people that self-medicate to the risk of infection from blood-borne diseases.

Even though the majority of injection devices used are the normal syringe the use of pen needle injectors is becoming more and more popular since they provide the possibility of an easy and convenient self-administration of drugs. The pen-type injectors are also becoming the only choice for certain types of drugs because they are not delivered in ordinary single use syringes.

In order to reduce the risk of accidental needle sticks, many pen injectors have been arranged with needle shields that are capable of covering said needle after injection. These needle shields may be useful but they add to the complexity and number of components of the injector. Further, if the injector is designed to deliver multiple doses, then the needle has to be replaced after each injection. This adds to the risk of accidental needle sticks and if the injector is arranged with a needle cover, this will be in the way when the needle is to be replaced.

A few safety pen needle solutions have been developed in order to minimize the risk of accidental needle sticks. One such solution is disclosed in the patent U.S. Pat. No. 7,462,168. Therein is described a safety pen needle with a passive safety shield system. It comprises a central hub to which an injection needle is attached, where the needle is provided with an injection end and a non-injection end, and where the latter is intended to penetrate a septum of a medicament container when mounted. Outside the hub, a sleeve is slidably arranged and further a shield is slidably arranged to the sleeve in a kind of telescopic manner. The sleeve and the shield are both urged in the proximal direction by a compression spring.

When the injection is performed the shield is pushed into the sleeve, which in turn slides in relation to the hub, thereby exposing the injection end of the needle. When the shield is fully depressed in relation to the sleeve, it becomes locked to the sleeve and they move in tandem during continued penetration. When the device is removed after injection, the sleeve and shield are moved in the proximal direction by the compression spring until tabs on the sleeve enter lock out recesses on the hub such that the sleeve and thus the shield are locked and the needle is protected.

Further the safety pen needle according to U.S. Pat. No. 7,462,168 comprises a safety system for the non-injection end of the needle. It comprises a non-injection end shield slidable in relation to the hub. A protrusion on the hub cooperates with tracks on the shield to first allow the shield to be pushed into the hub when mounted on a medicament container and then to lock said shield in an extended position when removed from the container, where the tracks have a first straight part and a latter inclined part with a depression for locking the shield.

However, probably functioning correctly in covering the needle, the safety pen needle according to '168 comprises a lot of interacting components in order to obtain the desired function, which makes the design rather difficult to manufacture and thereby rather costly.

Another solution is found in EP1289587B1 which discloses a disposable double pointed safety pen needle having a needle hub to which a thin needle cannula is permanently fastened and which needle hub can be mounted onto a syringe comprising a dose setting and injection mechanism and a cartridge containing a liquid medicine to be injected subcutaneously into a human body. The needle hub is provided with a safety shield guided on the outside surface of the needle hub. The safety shield is urged in a direction away from the needle hub by a spring located between the needle hub and the safety shield. The safety shield has a number of protrusions guided in guiding tracks on the outside surface of the needle hub. The guiding tracks are designed such that the safety shield during injection is displaced towards the needle hub by a translation movement and after injection is axially moved away from the needle hub by the spring and locked in an irreversible position where the safety shield covers the needle cannula and prevents accidental needle stick injuries. Since the shield is in contact with an injection site and the shield is moved by a translation movement, i.e. a rotationally axial displacement, the contact between the shield and the injection site i.e. the skin of a patient, is affected by a friction which may result in an ineffective function of the safety pen needle.

BRIEF DESCRIPTION OF THE INVENTION

A main aim of the present invention is to remedy the drawbacks of the safety pen needles of the state of the art and in particular to provide a safety pen needle device capable of performing a proper function with few components.

This aim is obtained by the features of the independent patent claim. Preferable embodiments of the invention form the subject of the dependent patent claims.

According to a major aspect of the invention, it is characterised by a safety pen needle device comprising a generally tubular hub having a proximal and a distal end, said hub comprising attachment means arranged at its distal end for attaching the safety pen needle device to a medicament container, and a coaxially arranged needle attachment member; an injection needle having an injection end and a non injection end, said injection needle being arranged extending through the needle attachment member; an actuation sleeve coaxially and rotationally positioned inside the proximal end of said hub; a generally tubular first needle shield having a proximal and a distal end, arranged surrounding the proximal end of said hub; first spring means coaxially arranged between said first needle shield and said actuation sleeve for urging said first needle shield in the proximal direction, such that said first needle shield covers the injection end of said needle; a second back-end needle shield coaxially arranged inside the distal end of said hub; second spring means coaxially arranged between said second needle shield and said hub for urging said second needle shield in the distal direction; wherein said second needle shield is provided with at least one first holding member arranged to cooperate with a corresponding at least one second holding member arranged on said actuation sleeve for holding said second needle shield in a position exposing said non-injection end of the needle in a pre-penetration state; wherein said first needle shield is provided with at least one first guide member arranged to cooperate with first guide tracks arranged on said actuation sleeve when said first needle shield is moved from an extended position surround said injection end of the needle to a retracted position, such that said actuation sleeve is rotated and thereby the at least one first holding member is released; wherein said hub is provided with at least one second guide member arranged to cooperate with second guide tracks arranged on said actuation sleeve when said first needle shield is moved from the extended position to the retracted position and vice versa, such that said when said first needle shield is moved from the retracted position to the extended position, the actuation sleeve is further rotated and thereby the at least one first guide member of the first needle shield abuts a first stop member arranged on said actuation sleeve for locking said first needle shield in the extended position.

According to another aspect of the invention, said second guide tracks and said second guide member are designed such that when said second needle shield is pushed towards the distal end, said actuation sleeve further rotates such that the least one first holding member abuts a second stop member arranged on said actuation sleeve for locking said second needle shield in a distal extended position covering the non injection end of the needle.

There are a number of advantages with the present invention. Because of first guide members coacting with first guide tracks, wherein an actuation sleeve is acting between the hub and the first needle shield, and because of the second guide members coacting with the second guide tracks, a safe and reliable locking of both the first and the second needle shield is obtained with very few components.

Thus the actuation sleeve is capable of both releasing the second needle shield, locking the first needle shield after withdrawal of the safety pen needle and locking of the second needle shield after removal of the safety pen needle. Thus the actuation sleeve performs a number of functions in cooperation with the needle shields and the hub, thus requiring few components.

There is thus provided a reliable and functional safety pen needle comprising a small number of components, thereby keeping the production costs at low levels.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
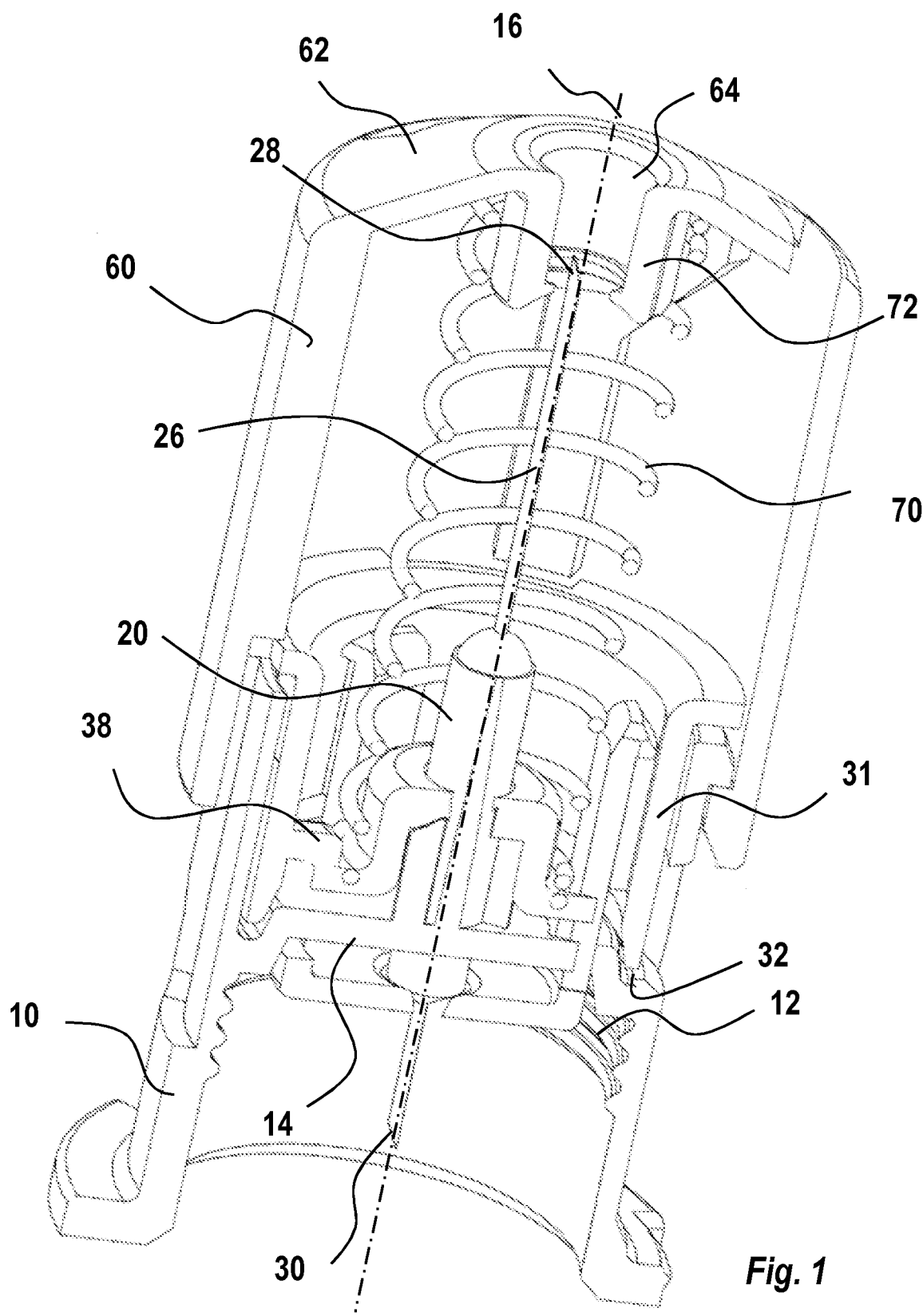
FIG. 1 shows a cross-sectional side view of a safety pen needle device according to the present invention in an initial position.

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the medicament delivery device is located closest to the medicament delivery site of the patient.

The embodiment of the present invention shown in the drawings, which is intended to be used with a medicament delivery device, comprises:

a generally tubular hub 10 having a proximal and a distal end, said hub comprising attachment means 12 arranged at its distal end for attaching the safety pen needle device to a medicament container, and a coaxially arranged needle attachment member 20;

an injection needle 26 having an injection end 28 and a non injection end 30, said injection needle being arranged extending through the needle attachment member;

an actuation sleeve 31 coaxially and rotationally positioned inside the proximal end of said hub;

a generally tubular first needle shield 60 having a proximal and a distal end, arranged surrounding the proximal end of said hub;

first spring means 70 coaxially arranged between said first needle shield and said actuation sleeve for urging said first needle shield in the proximal direction, such that said first needle shield covers the injection end of said needle;

a second back-end needle shield 90 coaxially arranged inside the distal end of said hub;

second spring means 102 coaxially arranged between said second needle shield and said hub for urging said second needle shield in the distal direction; wherein said second needle shield is provided with at least one first holding member 96,98 arranged to cooperate with a corresponding at least one second holding member 50,100 arranged on said actuation sleeve for holding said second needle shield in a position exposing said non-injection end of the needle in a pre-penetration state;

said first needle shield is provided with at least one first guide member 74,77 arranged to cooperate with first guide tracks 36 arranged on said actuation sleeve when said first needle shield is moved from an extended position surround said injection end of the needle to a retracted position, such that said actuation sleeve is rotated and thereby the at least one first holding member is released;

said hub is provided with at least one second guide member 22, 24 arranged to cooperate with second guide tracks 42 arranged on said actuation sleeve when said first needle shield is moved from the extended position to the retracted position and vice versa, such that said when said first needle shield is moved from the retracted position to the extended position, the actuation sleeve is further rotated and thereby the at least one first guide member of the first needle shield abuts a first stop member 34 arranged on said actuation sleeve for locking said first needle shield in the extended position.

Figure 2:
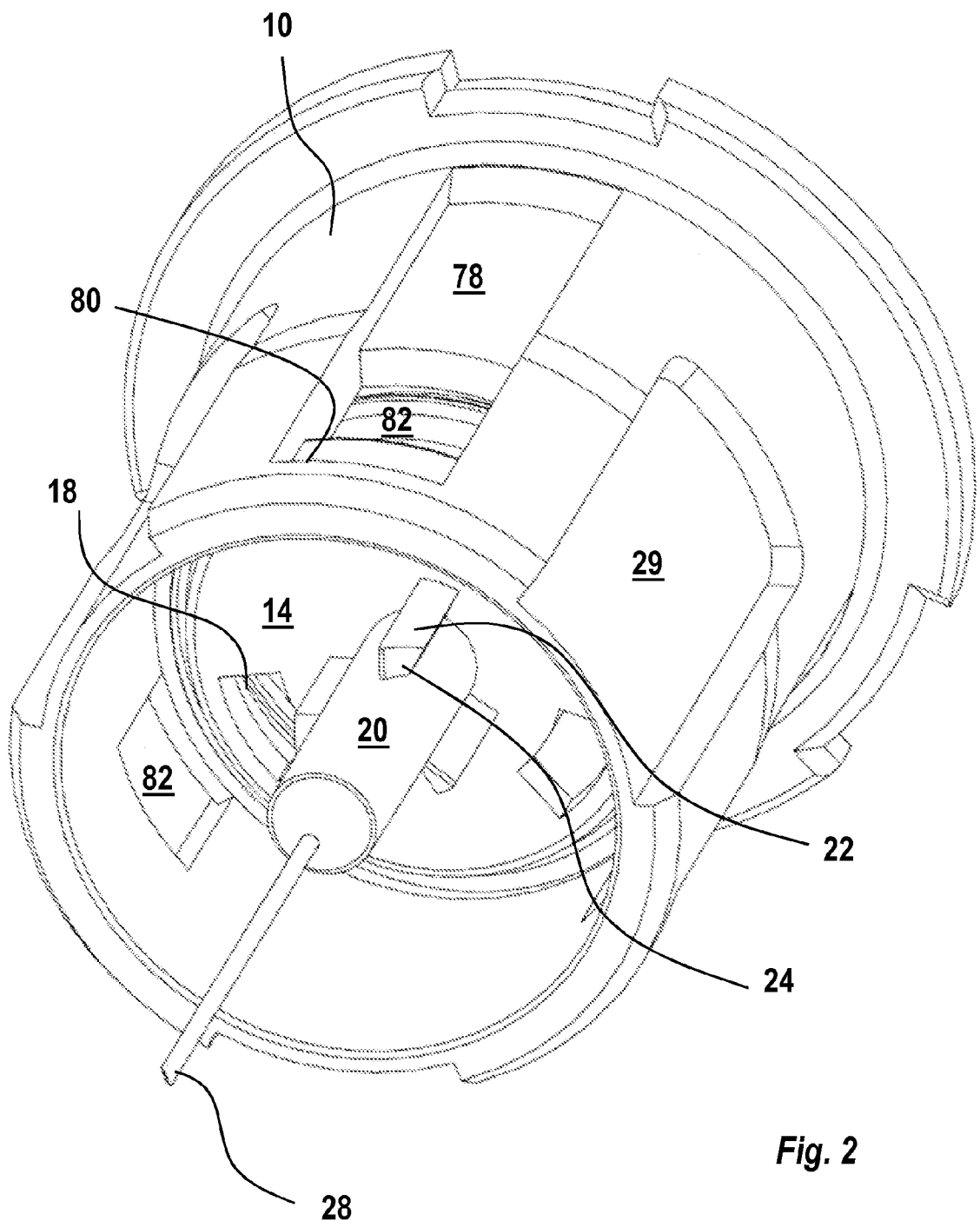
FIG. 2 shows a detailed perspective view of a hub comprised in the present invention.
Figure 3:
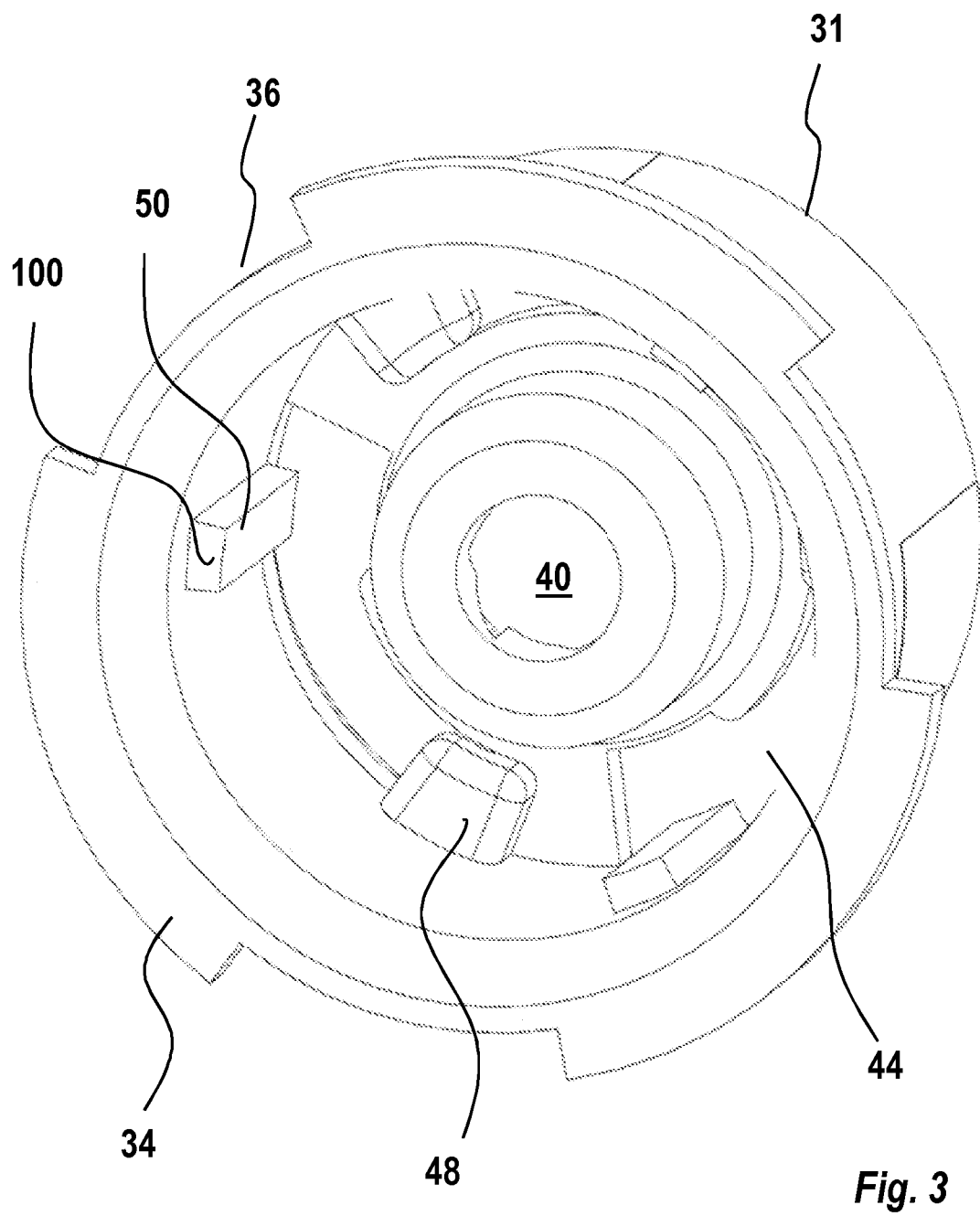
FIG. 3 shows a detailed perspective view of an actuating sleeve comprised in the present invention.

An inner circumferential surface of the hub at the distal end thereof is arranged with the engagement means such as threads 12, which are arranged to cooperate with corresponding engagement means such as threads of a medicament container or of a container housing (not shown). A wall 14 is attached to, or made integral with, the inner surface of the hub 10 and extending generally transversal in relation to a longitudinal direction 16 of the device. The wall is provided with a number of passages 18, FIG. 2. The needle attachment member 20 is arranged to, or made integral with, said end wall 14, where the needle attachment member 20 has a generally cylindrical shape. The second guide members as a number of ledges 22 where each ledge 22 is provided with a proximally directed surface 24 having a certain inclination, are attached to or made integral with, the needle attachment member, FIG. 2.

In the centre of the needle attachment member, the hollow injection needle 26 is attached. The injection needle 26 is provided with the proximal pointed injection end 28 and the distal pointed non-injection end 30, where the latter is arranged to penetrate a septum of the medicament container in order to provide a passage from the container through the needle 26 to the proximal injection end 28. The outer side surface of the hub is further provided with cut-outs 29 having a certain width in the circumferential direction, FIG. 2.

The actuation sleeve 31, which is arranged to the hub 10, comprises a generally cylindrical shape having an outer diameter which is somewhat smaller than the diameter of the proximal part of the hub such that the hub surrounds the proximal part of the actuation sleeve, where the distal end surface 32 of the actuation sleeve 31 is in contact with a side surface of the wall 14.

The actuation sleeve is further provided with the first stop member as a circumferential, radial and outwardly directed ledge 34, which ledge is arranged with the first guide tracks as a number of cut-outs 36. The actuation sleeve is further arranged with a wall 38 extending transversally in relation to the longitudinal direction 16 of the device. The wall 38 is provided with a central passage 40, through which passage 40 the needle attachment member 20 protrudes. Further, the second guide tracks as a number of distally directed inclined surfaces 42 surround the central passage 40, FIG. 4, intended to cooperate with the inclined surfaces 24 of the hub in a manner that will be described. The wall 38 is further provided with a number of passages 44, each having a generally arc-shaped extension. At one end of the arc-shaped passages 44 a second stop member as a step formed ledge 48 is arranged displaced somewhat in the proximal direction, FIG. 4. Further, the second holding members as elongated ledges 50 are arranged on the inner surface of the actuation sleeve extending in the longitudinal direction 16, FIG. 5.

Figure 5:
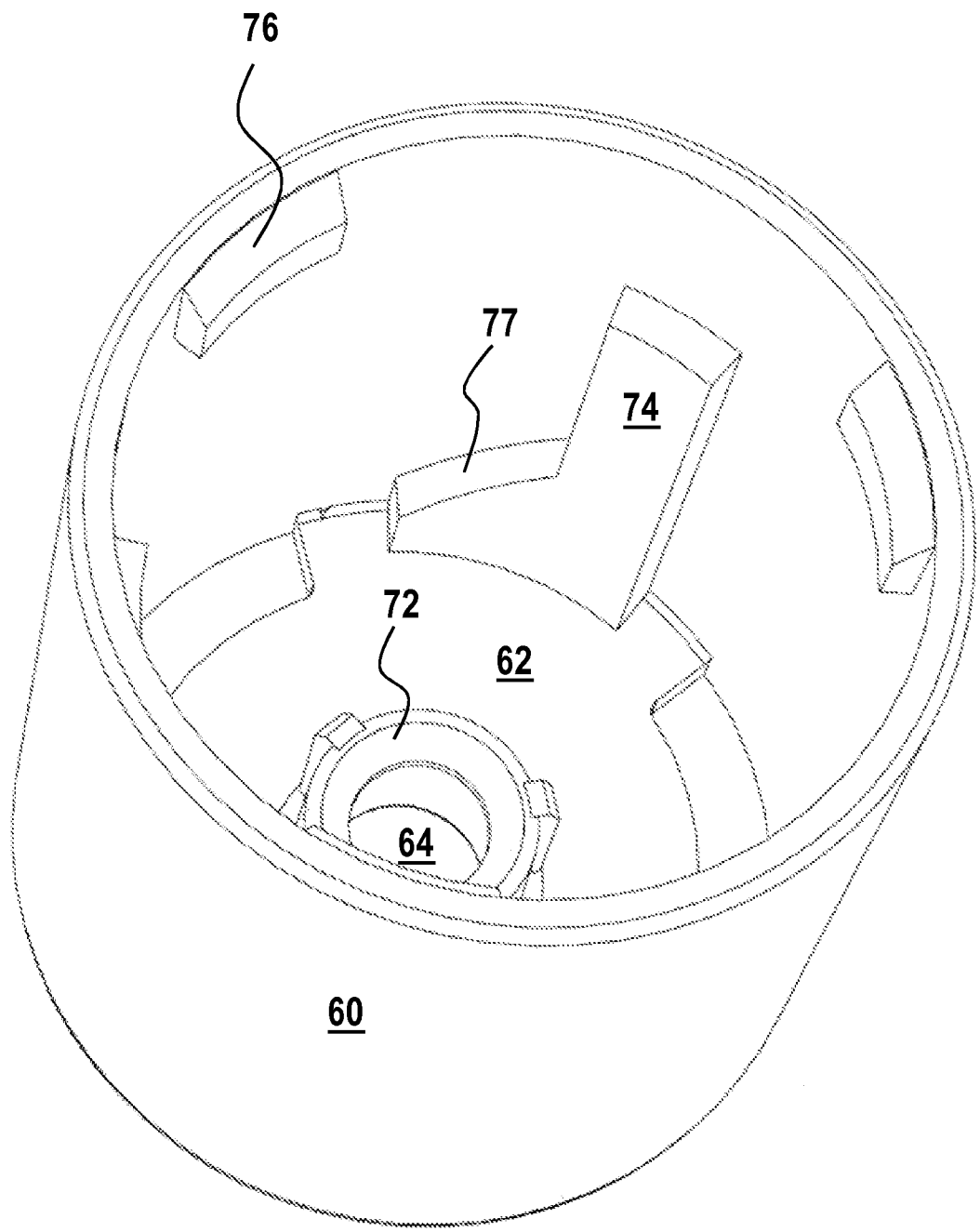
FIG. 5 shows a detailed perspective view of a first needle shield comprised in the present invention.
Figure 6:
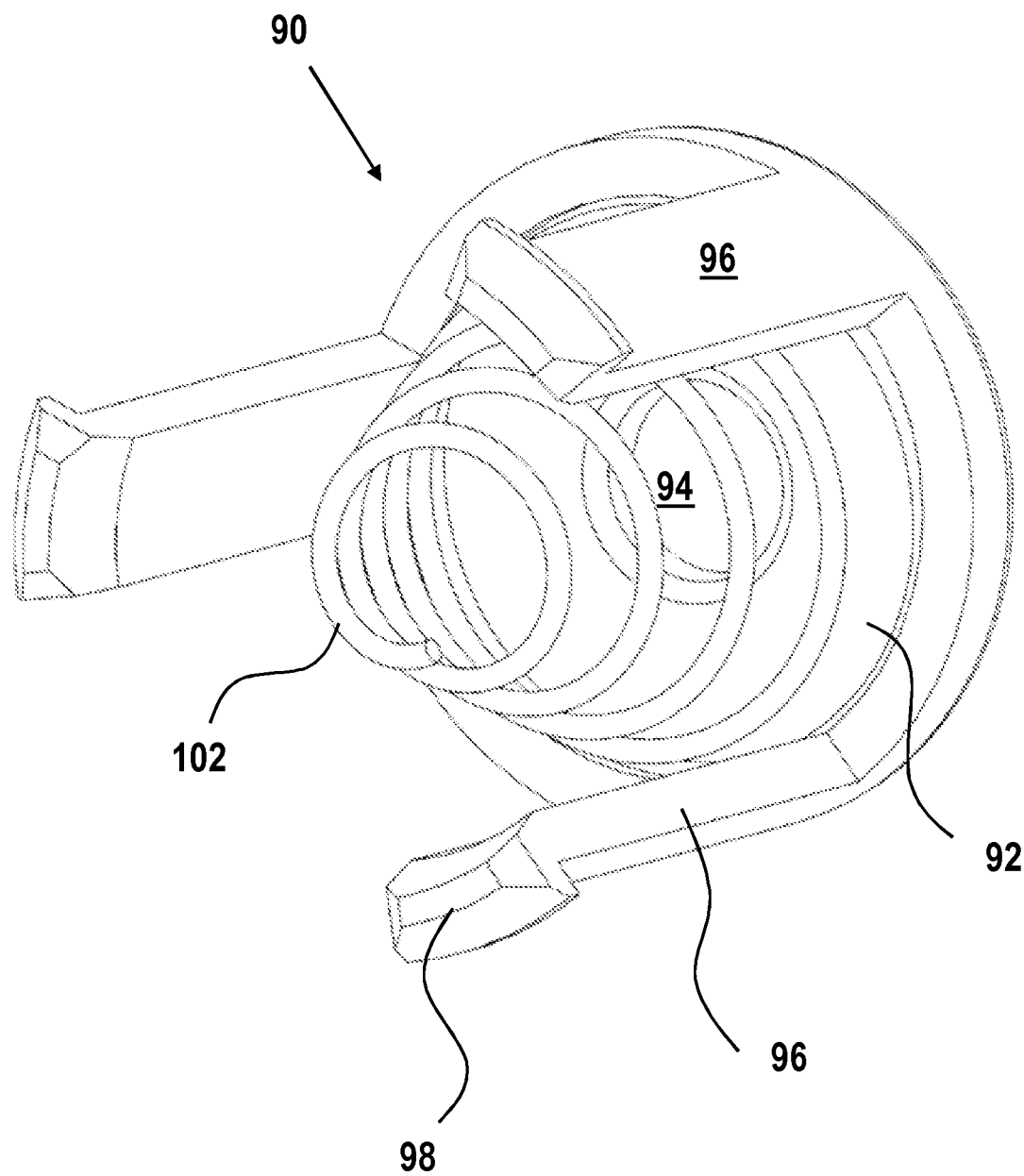
FIG. 6 shows a detailed perspective view of a back-end needle shield comprised in the present invention.

The first needle shield 60, FIG. 5, comprises a generally tubular part having a diameter somewhat larger than the outer diameter of the hub 10. The proximal end of the first needle shield 60 is arranged with an end wall 62, which end wall is provided with a central opening 64 through which the proximal end 28 of the injection needle 26 may pass. The first spring means such as a compression spring 70 is arranged between a guide part of the wall 38 of the actuation sleeve 30 and the inner surface of the end wall 62 of the first needle shield 60, which is provided with a generally tubular guide part 72 extending towards the proximal direction, FIG. 1.

On the inner surface of the first needle shield 60, the first guide members such as a number of elongated ledges 74 with an extension having an inclined surface 77 are arranged, having positions such that they fit into the cut-outs 29 on the outer surface of the hub when mounted. Further, in order to hold the first needle shield in relation to the hub, a number of circumferentially directed ledges 76 are attached to, or made integral with, the inner surface of the first needle shield in the distal area thereof, which ledges 76 are arranged to fit into elongated cut-outs 78 in the outer surface of the hub, which cut-outs 78 end at a certain distance before the proximal end surface, providing stop ledges 80 for the ledges 76 of the first needle shield. The cut-outs 78 in the hub are further provided with passages 82, the function of which will be described below.

The second needle shield such as a second back-end needle shield 90 protects the non-injection pointed end of the needle. It comprises a plate-like body 92 with a central opening 94 and the first holding members such as a number of arms 96 extending in the proximal direction and where each arm is provided with a radially outwardly directed ledge 98 having an inclined surface in the proximal direction. The second spring means such as a spring 102 is arranged between the body 92 and a distal side surface of the wall 14 for urging the back-end needle shield 90 in the distal direction.

Figure 7:
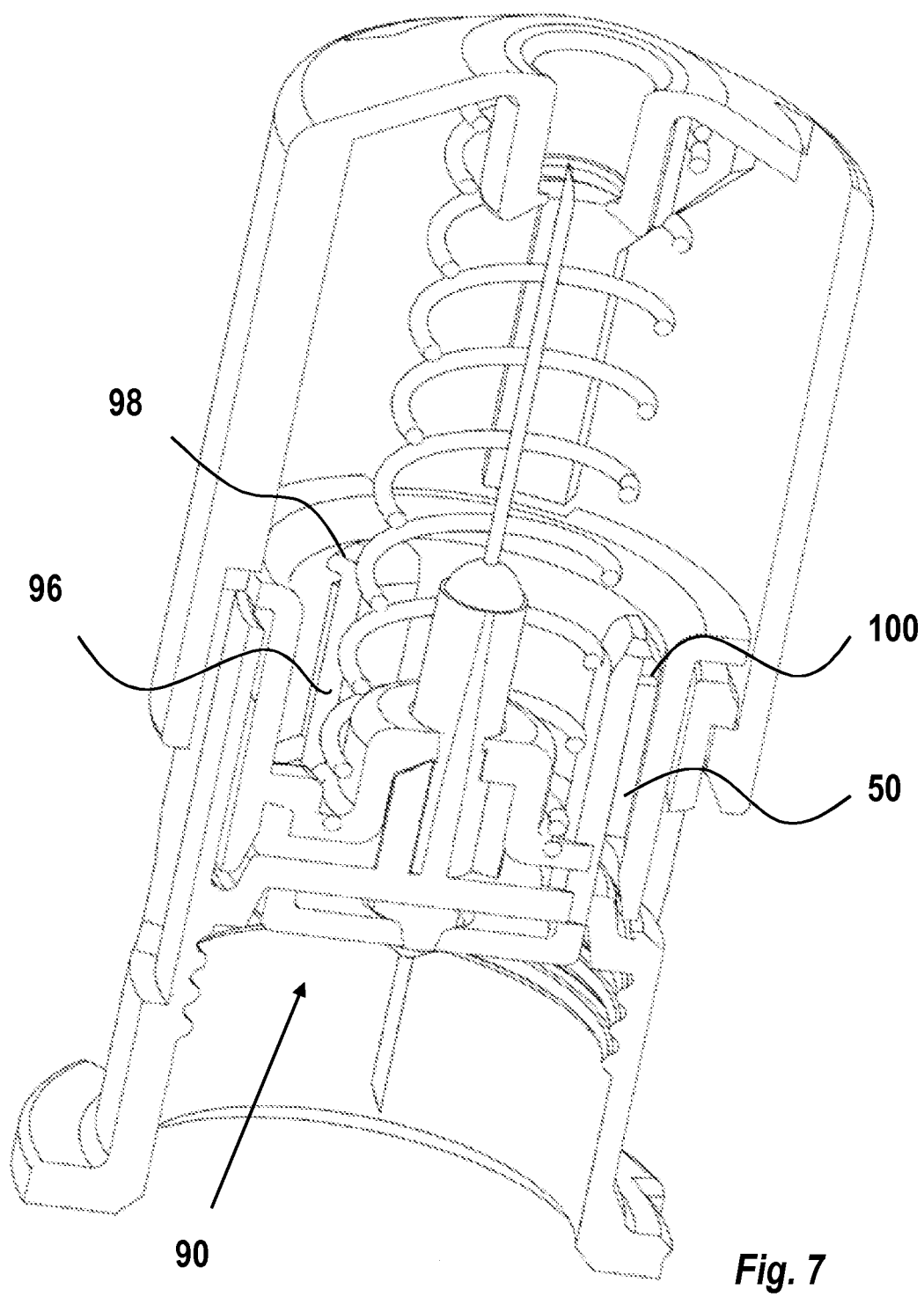
FIGS. 7-11 show different functional states of the safety needle according to the present invention.

The device is intended to function as follows. When the device is delivered to the user it has an appearance as in FIG. 1, wherein the proximal pointed injection end 28 of the needle is protected by the first needle shield 60. The first needle shield 60 is urged in the proximal direction by the spring 70 but stopped by the ledges 76 of the first needle shield abutting the ledges 80 of the cut-outs 79. The back end needle shield 90 is held in a suspended position as shown in FIG. 1, wherein the ledges 98 of the arms 96 are in contact with a proximal end surface 100 of the elongated ledges 50 of the actuation sleeve. When an injection is to be performed, the hub 10 is attached onto a neck of a medicament container or of a container housing such that the non-injection end 30 of the needle penetrates a septum of the medicament container. In this respect, it is to be understood that the attachment means could be other than threads, such as for example bayonet fittings, snap-on mechanisms and the like. The back end needle shield 90 is pushed somewhat in the proximal direction during the attachment of the device so that the ledges 98 are moved out of contact with the surfaces 100, FIG. 7.

Figure 8:
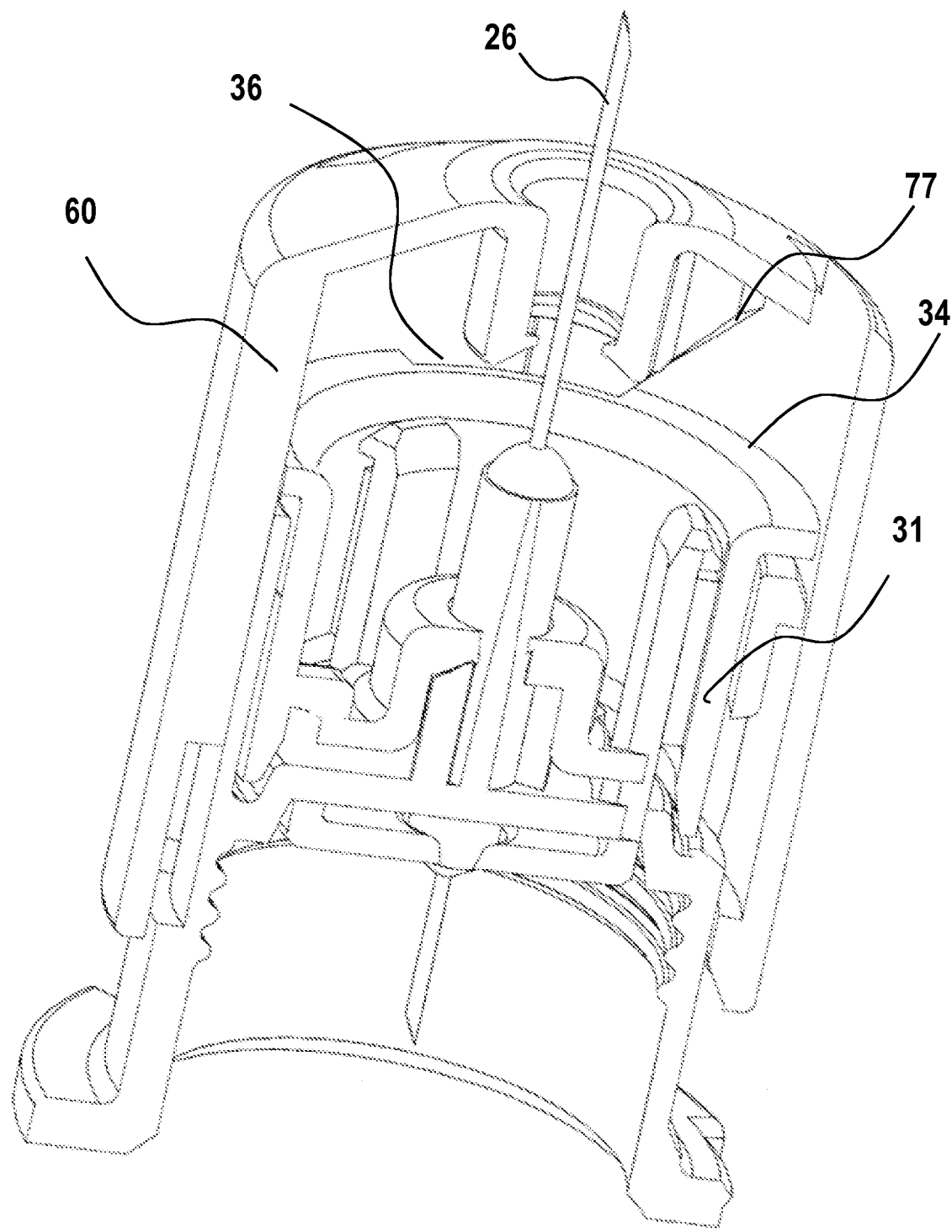
Figure 9:
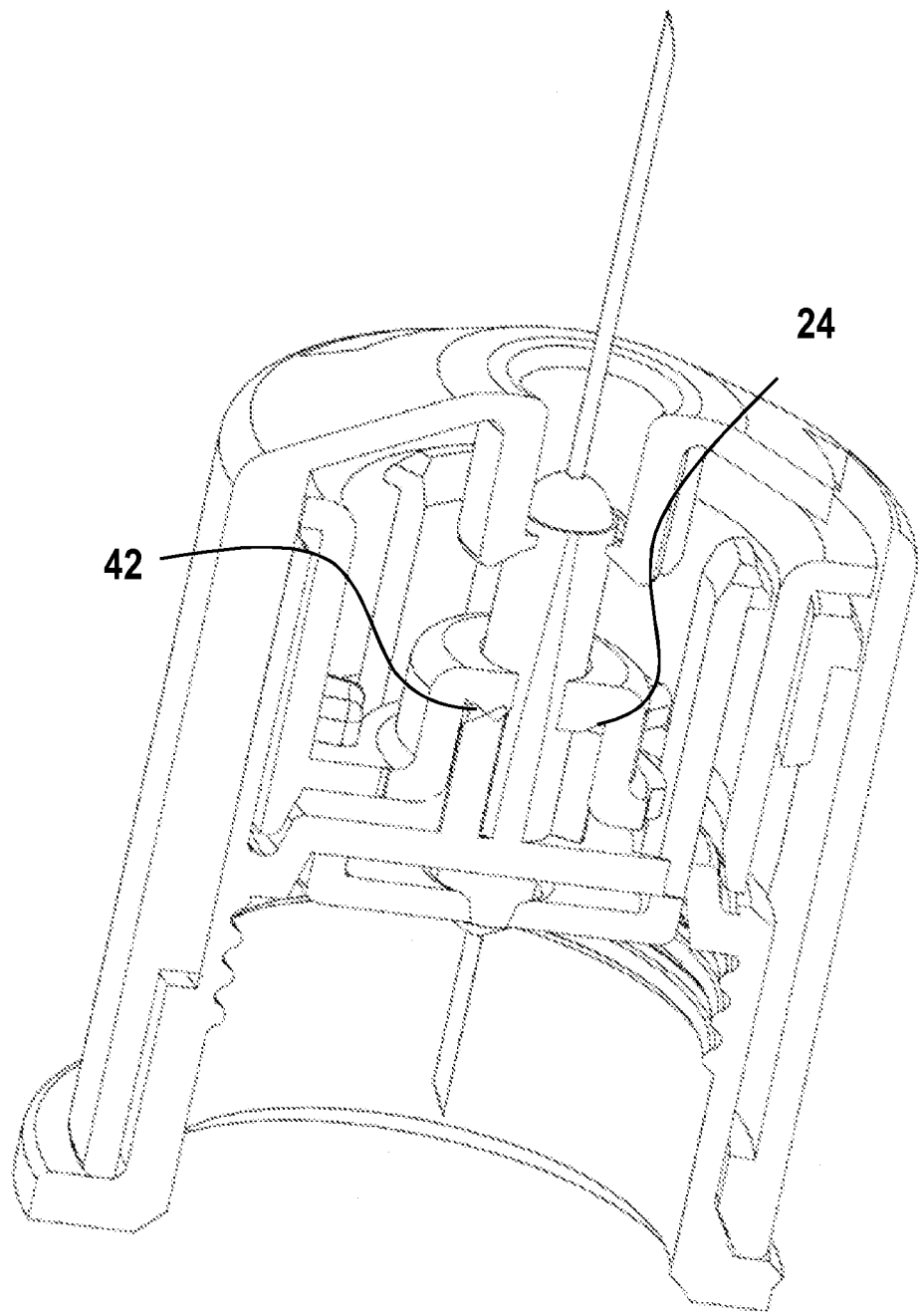

A penetration and subsequent injection may now be performed. The proximal part of the device is thus pressed against the injection site, wherein the first needle shield is moved from the extended position to the retracted position. This causes the first needle shield 60 to be pushed in the distal direction against the force of the spring 70, whereby a penetration by the needle 26 is initiated, FIG. 8. When the first needle shield has reached a certain position in relation to the hub, the inclined surfaces 77 of the first needle shield will come in contact with a side edge of the cut-outs 36 on the circumferential ledge 34 of the actuation sleeve 31 whereby the latter will rotate in relation to the hub. The rotation of the actuation sleeve causes the ledges 98 of the back-end needle shield to move out of alignment with the ledges 50. The rotation of the actuation sleeve also causes the inclined surfaces 42 of the actuation sleeve to move in relation to the inclined surfaces 24 of the ledges 22 of the hub. FIG. 9 shows a full penetration.

Figure 4:
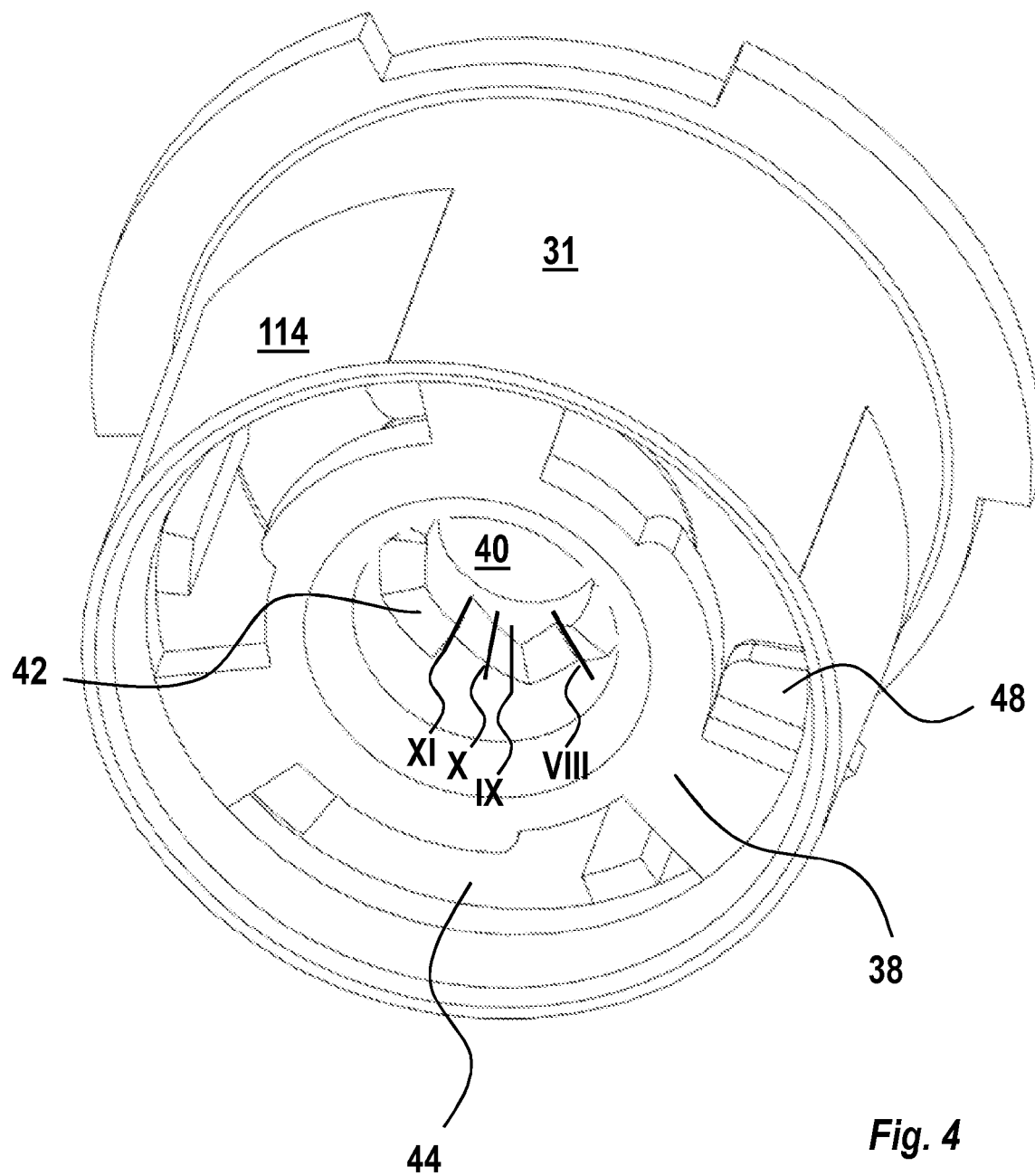
FIG. 4 shows the actuating sleeve of FIG. 3 turned 180°.
Figure 10:
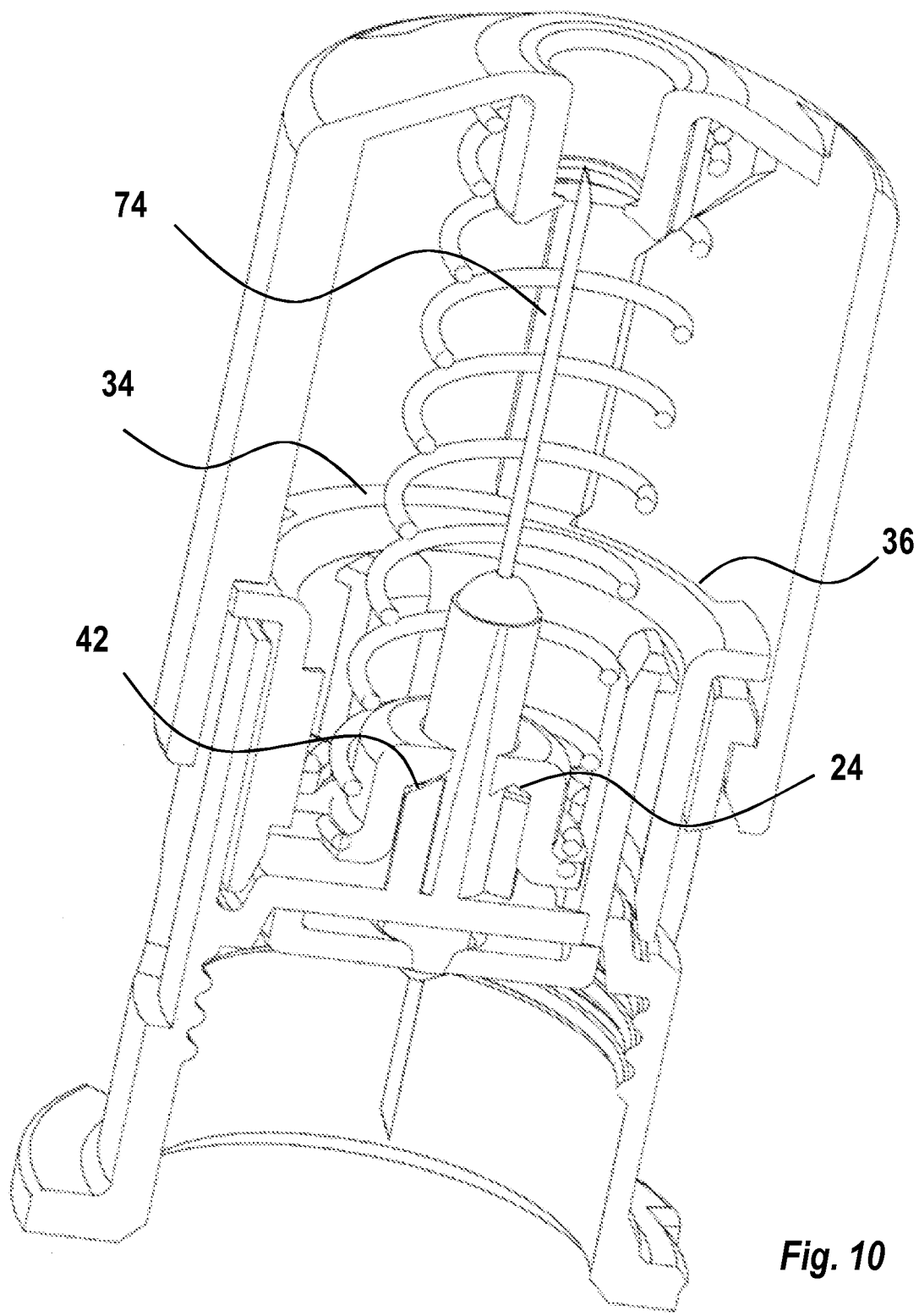
Figure 11:
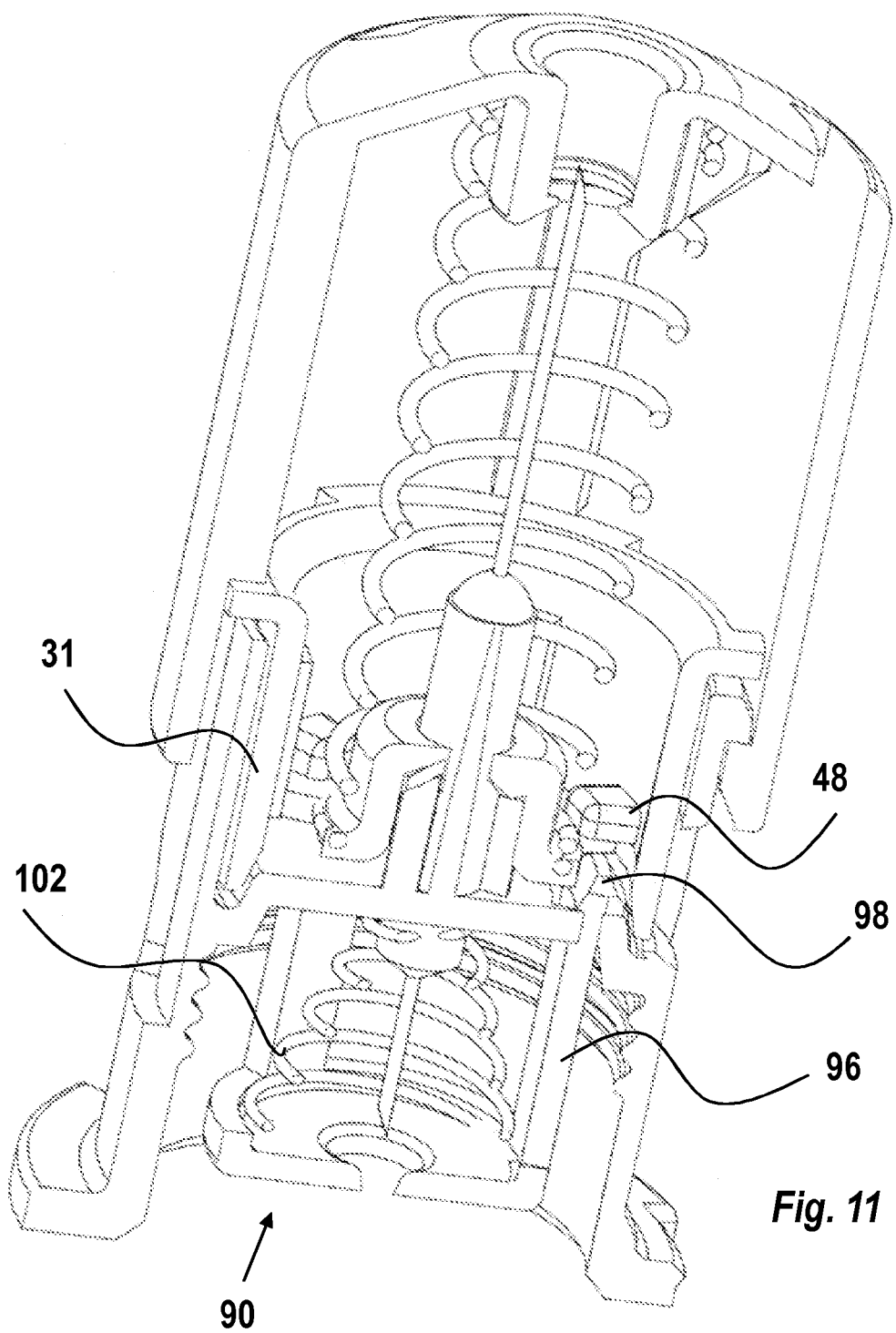

When the injection has been performed, the user withdraws the injector from the injection site, wherein the first needle shield is moved from the retracted position to the extended position. This causes the first needle shield 60 to be pushed in the proximal direction by the spring 70 in relation to the hub 10, FIG. 10. The actuation sleeve tries to turn in the clockwise direction due to the positions of the inclined surfaces 24 and 42 but is prevented because a side surface of the elongated ledges 74 is in contact with a side surface of the cut-outs 36 of the actuation sleeve until the first needle shield has extended such that the ledge 74 is moved out of contact with the cut-out. The actuation sleeve is now free to rotate a certain distance whereby the ledge 34 of the actuation sleeve is moved under the ledge 74 of the first needle shield, FIG. 10. This causes the first needle shield to be locked from being moved in the distal direction and thereby any accidental needle sticks are prevented. The device may now be removed from the injector and discarded. When removing the device, the back-end needle shield 90 moves in the distal direction due to the spring 102. A side surface of the arms 96 of the back end needle shield has come in contact with a side surface of the ledge 48 during the previously described turning of the actuation sleeve. When now the back-end needle shield is moved in the distal direction, the arms 96 are moved out of contact with the actuation sleeve, whereby it is free to rotate a certain distance further as seen in FIG. 4, whereby the ledge 48 is moved above the ledge 98 of the arms 96 of the back-end needle shield 90, FIG. 11. Thereby, also the back-end needle shield is locked from being moved in the proximal direction, and thereby any accidental needle sticks on the non-injection end of the needle are prevented. The device could further be arranged with visual means such as areas 114 with different colour on the actuation sleeve that during the rotation of the actuation sleeve, FIG. 4, during penetration and subsequent locking of the first needle shield causes the areas 114 to be aligned with the passages 82 on the hub 10.

It is to be understood that the embodiments described above and shown in the drawings only are to be regarded as non-limiting examples of the invention and that it may be modified in many ways within the scope of the patent claims.

For example, instead of an end wall 62 the proximal end of the first needle shield may be completely open. The resilient means 70 will then be arranged to act on an appropriate ledge or wall of the distal part of the first needle shield. In this aspect it is conceivable to have initial locking means that lock the first needle shield to the hub before the safety pen needle is used. The initial locking means may comprise a bayonet fitting such that the user twists the first needle shield a certain angle in relation to the hub until the first needle shield is free to be pushed into the hub during penetration as described above.

As a further development of the invention the device could further comprise a cap having a proximal and a distal end and arranged to cover said first needle shield and said hub. According to one aspect the cap could comprise two parts releasibly connectable to each other by e.g. threads or bayonet fittings or an open cap and some form of sealing means, such as a metal foil or plastic film or the like, arranged on the distal end of the cap for avoiding contamination of the non injection end of the injection needle.

The invention claimed is:

1. A safety pen needle device, comprising:
   a generally tubular hub having a proximal, a distal end, an attachment device arranged at the distal end and configured for attaching the safety pen needle device to a medicament container, and a coaxially arranged needle attachment member;
   an injection needle having an injection end and a non-injection end, and extending through the needle attachment member;
   an actuation sleeve coaxially and rotationally positioned inside the proximal end of the hub;
   a generally tubular first needle shield having a proximal and a distal end and surrounding the proximal end of the hub;
   a first spring device coaxially arranged between the first needle shield and the actuation sleeve for urging the first needle shield in the proximal direction, such that the first needle shield covers the injection end of the needle;
   a second back-end needle shield coaxially arranged inside the distal end of the hub; and
   a second spring device coaxially arranged between the second needle shield and the hub for urging the second needle shield in the distal direction;
   wherein the second needle shield includes at least one first holding member configured to cooperate with a corresponding at least one second holding member arranged on the actuation sleeve for holding the second needle shield in a position exposing the non-injection end of the needle in a pre-penetration state;
   the first needle shield includes at least one first guide member configured to cooperate with at least one first guide track arranged on the actuation sleeve when the first needle shield is moved from an extended position surrounding the injection end of the needle to a retracted position, such that the actuation sleeve is rotated and thereby the at least one first holding member is released; and
   the hub includes at least one second guide member configured to cooperate with at least one second guide track arranged on the actuation sleeve when the first needle shield is moved from the extended position to the retracted position and vice versa, such that when the first needle shield is moved from the retracted position to the extended position, the actuation sleeve is further rotated and thereby the at least one first guide member of the first needle shield abuts a first stop member arranged on the actuation sleeve for locking the first needle shield in the extended position.

2. The safety pen needle device of claim 1, wherein the at least one first guide track includes at least one section that is inclined in relation to a longitudinal direction of the safety pen needle device and at least one section that is parallel in relation to the longitudinal direction of the device, and the at least one section that is inclined and the at least one first guide track forces the actuation sleeve to rotate.

3. The safety pen needle device of claim 1, wherein the first needle shield includes an end wall having a central opening configured for passing the injection end of the injection needle.

4. The safety pen needle device of claim 1, wherein the at least one second guide track and second guide member are configured such that when the second needle shield is pushed toward the distal end, the actuation sleeve further rotates such that the least one first holding member abuts a second stop member arranged on the actuation sleeve for locking the second needle shield in a distal extended position covering the non-injection end of the needle.

5. The safety pen needle device of claim 4, wherein the first needle shield includes an end wall having a central opening configured for passing the injection end of the injection needle.

6. The safety pen needle device of claim 4, wherein the at least one first guide track includes at least one section that is inclined in relation to a longitudinal direction of the safety pen needle device and at least one section that is parallel in relation to the longitudinal direction of the device, and the at least one section that is inclined and the at least one first guide track forces the actuation sleeve to rotate.

7. The safety pen needle device of claim 6, wherein the first needle shield includes an end wall having a central opening configured for passing the injection end of the injection needle.

* * * * *